United States Patent
Frassetto et al.

(10) Patent No.: US 12,338,195 B2
(45) Date of Patent: Jun. 24, 2025

(54) PROCESS FOR THE PREPARATION OF 1-[4-NITRO-2-(TRIFLUOROMETHYL) PHENYL]-ALKANONES

(71) Applicant: BASF AGRO B.V., Arnhem (NL)

(72) Inventors: Timo Frassetto, Ludwigshafen (DE); Florian Vogt, Ludwigshafen (DE); Christiane Alznauer, Ludwigshafen (DE); Sebastian Illies, Ludwigshafen (DE); Philip Muelheims, Ludwigshafen (DE); Swapnil Yerande, Pune (IN); Daniel Saelinger, Ludwigshafen (DE); Robin Thiele, Ludwigshafen (DE); Heinz Friedrich Sutoris, Limburgerhof (DE); Marcel Hofrichter, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 418 days.

(21) Appl. No.: 17/797,536

(22) PCT Filed: Feb. 2, 2021

(86) PCT No.: PCT/EP2021/052394
§ 371 (c)(1),
(2) Date: Aug. 4, 2022

(87) PCT Pub. No.: WO2021/160468
PCT Pub. Date: Aug. 19, 2021

(65) Prior Publication Data
US 2023/0091355 A1    Mar. 23, 2023

(30) Foreign Application Priority Data

Feb. 13, 2020 (EP) .................................. 20157207

(51) Int. Cl.
C07C 201/12  (2006.01)
C07C 45/64   (2006.01)

(52) U.S. Cl.
CPC ............ *C07C 201/12* (2013.01); *C07C 45/64* (2013.01)

(58) Field of Classification Search
CPC ........ C07C 45/64; C07C 49/76; C07C 203/02
See application file for complete search history.

(56) References Cited

FOREIGN PATENT DOCUMENTS

| GB | 804467 A | * | 11/1958 | |
|----|----------|---|---------|---|
| WO | WO-2018/102751 A1 | | 6/2018 | |
| WO | WO-2018215668 A1 | * | 11/2018 | ......... A61K 31/5383 |

OTHER PUBLICATIONS

A. L. Shul'tsev, 83 (4) Russian Journal of General Chemistry, 773-774, (2013) (Year: 2013).*
European Search Report for EP Patent Application No. 20157207.0, Issued on Aug. 11, 2020, 3 pages.
International Application No. PCT/EP2021/052394, International Search Report and Written Opinion, mailed Apr. 13, 2021.
Kornblum, et al., "A new and convenient synthesis of glyoxals, glyoxalate esters, and α-diketones", Journal of the American Chemical Society, vol. 88, Issue 4, Feb. 1, 1966, pp. 865-866.
Letsinger, et al., "Synthesis of Pyranones and Benzofluorenones from Ketones and Carboxylic Acids", Journal of the American Chemical Society, vol. 83, Issue 1, Jan. 1, 1961, pp. 193-198.
Shul'tsev, Synthesis of aromatic ketones, Russian J. General Chemistry, 83(4):773-7 (Apr. 2013).
Teng, et al., "Synthesis and characterization of trifluoromethyl substituted styrene polymers and copolymers with methacrylates: Effects of trifluoromethyl substituent on styrene", Polymer, vol. 52, Issue 4, Feb. 17, 2011, pp. 949-953.
Wu, et al., "Synthesis of 4(5)-nitroimidazole-5(4)-carboxaldehyde by oxidative elimination of a nitrate ester", The Journal of Organic Chemistry, vol. 47, Issue 13, Jun. 1, 1982, pp. 2661-2663.

* cited by examiner

*Primary Examiner* — Alexander R Pagano
*Assistant Examiner* — Frank S. Hou
(74) *Attorney, Agent, or Firm* — MARSHALL, GERSTEIN & BORUN LLP

(57) ABSTRACT

The present invention relates to a process for the preparation of 1-[4-nitro-2-(trifluoromethyl)-phenyl]-alkanones and substituted phenoxyphenyl ketones.

13 Claims, No Drawings

PROCESS FOR THE PREPARATION OF 1-[4-NITRO-2-(TRIFLUOROMETHYL) PHENYL]-ALKANONES

CROSS-REFERENCE TO RELATED APPLICATIONS

This is the U.S. national phase of International Application No. PCT/EP2021/052394, filed Feb. 2, 2021, which claims the benefit of European Patent Application No. 20157207.0, filed on Feb. 13, 2020.

The present invention relates to a process for the preparation of 1-[4-nitro-2-(trifluoromethyl)-phenyl]-alkanones and substituted phenoxyphenyl ketones.

1-[4-nitro-2-(trifluoromethyl)phenyl]alkanones (I) are valuable substrates for the synthesis of pesticidally active compounds. Therefore, there is a need for processes that easily make it available.

One of the ways for preparing such ketones is the treating of the respective nitrate esters with a base.

The use of the bases for conversion of nitrates to aldehydes or ketones is described e.g. in *Russian Journal of General Chemistry*, 2013, 83 (4), pp. 773-774 (NaOEt in ethanol); *J. Am. Chem. Soc*, 1966, 88(4), pp. 865-866 (NaOAc in DMSO); *J. Am. Chem. Soc.* 1961, 83(1), 193-198 (KOH in water/dioxane), *JOC*, 1982, 47(13), pp. 2661-2663 (DBN in chloroform).

However, the described processes are not useful for an industrial scale because either the yield is not sufficient, or reaction conditions or parameters are not suitable. The organic bases, like DBN, are rather expensive to be used alone and, therefore, must be recovered. The use of inorganic hydroxide bases in water miscible solvents leads to the formation of undesired byproducts, like phenols, benzylic alcohols or aldol reaction products. The reaction in water immiscible solvents or solvents that are sparingly soluble in water is slow and the addition of phase transfer catalysts also results in the formation of by-products. Additionally, the nitrated aromatic starting material must be handled carefully because of it's explosivity or shock sensitivity.

Therefore, it was an object of the present invention to develop a process for the preparation of 1-[4-nitro-2-(trifluoromethyl)phenyl]-alkanones (I), which process is efficient, safe and leads to the desired product in high yield, hence being suitable for an upscale to industrially relevant amounts. In one specific aspect, it should be possible to use the starting material coming directly from its preparation step without extensive work up and/or without solvent exchange.

It has now surprisingly been found a highly efficient process for preparation of 1-[4-nitro-2-(trifluoromethyl)phenyl]-alkanones (I) in high yields.

Accordingly, the present invention relates to a process for the preparation of the compound of formula (I)

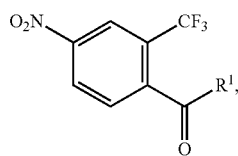

wherein $R^1$ is $C_1$-$C_4$-alkyl;

comprising the following step:
(i) reacting a compound of formula (II)

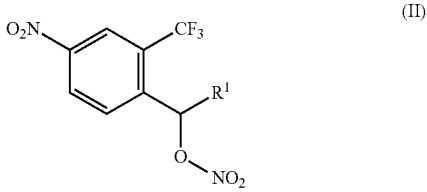

with an aqueous solution of an inorganic base selected from hydroxides, carbonates or phosphates of alkali or earth alkali metals, or aluminium hydroxide or any mixtures thereof in the presence of an organic base selected from amidine and guanidine bases, in an inert organic solvent, wherein the reaction is heterophase and the organic base is used in an amount of 0.001 to 0.3 mol equivalents per 1 mol of compound (II).

The term "$C_1$-$C_4$-alkyl" refers to a straight-chained or branched saturated hydrocarbon group having 1 to 4 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl or 3-methylbutyl.

The process according to the present invention entails a series of advantages. It is safe, cheap, fast and leads to the product in high yields, thus being suitable for an industrial production. Undesired side reactions leading to unwanted by-products are minimized.

Further embodiments of the invention are evident from the claims, the description and the examples. It is to be understood that the single features of the subject matter of the invention described herein can be applied not only in the combination given in each particular case but also in other combinations, without leaving the scope of the invention.

Starting compound (II) can be synthesized as known to the skilled person or as described herein below.

The step (i) according to the present invention can be carried out batchwise or continuously. According to one embodiment, it is carried out batchwise. According to another embodiment, it is carried out continuously.

The step (i) is carried out in the presence of an inorganic base and an organic base.

The inorganic base is preferably selected from hydroxides, carbonates or phosphates of alkali or earth alkali metals, or aluminium hydroxide, or any mixtures thereof. Examples of the suitable inorganic bases are NaOH, KOH, CsOH, $Na_2CO_3$, $K_2CO_3$, $Cs_2CO_3$, $Na_3PO_4$, $K_3PO_4$, $Al(OH)_3$.

According to one embodiment, the inorganic base is selected from hydroxides of alkali or earth alkali metals, preferably from KOH, NaOH or CsOH. According to one embodiment, the inorganic base is KOH. According to another embodiment, the inorganic base is NaOH. According to another embodiment, the inorganic base is CsOH.

According to another embodiment, the inorganic base is selected from carbonates of alkali or earth alkali metals, such as $Na_2CO_3$, $K_2CO_3$, or $Cs_2CO_3$. According to one specific embodiment, the inorganic base is $Na_2CO_3$. According to another specific embodiment, the inorganic base is $K_2CO_3$. According to another specific embodiment, the inorganic base is $Cs_2CO_3$.

According to another embodiment, the inorganic base is selected from phosphates of alkali or earth alkali metals, such as $Na_3PO_4$, or $K_3PO_4$. According to one specific embodiment, the inorganic base is $Na_3PO_4$. According to another specific embodiment, the inorganic base is $Na_3PO_4$, or $K_3PO_4$.

According to another embodiment, the inorganic base is $Al(OH)_3$.

The inorganic base is preferably used in an amount of at least 0.5 mole equivalents, more preferably at least 0.7 mole equivalents, most preferably at least 1 mole equivalents, in particular at least 1.1 mole equivalents per 1 mole of compound (I). The molar ratio of the inorganic base and compound (II) is generally in the range from 0.7:1 to 5:1, preferably from 0.7:1 to 4:1, more preferably from 0.8:1 to 3:1, most preferably from 1:1 to 2.5:1. The molar ratio of the inorganic base to compound (II) can also be in the range from 1:1 to 2:1.

The inorganic base is used as an aqueous solution. The concentration of the aqueous solution is usually from 2 to 80 wt %, preferably from 10 to 60 wt %, more preferably from 20 to 50 wt %. The concentration is preferably adjusted in a way that the inorganic base and the nitrite salts formed in the reaction course remain dissolved in the reaction mixture.

The organic base is selected from amidine and guanidine bases. Said bases preferably have the general formula (B1) or (B2)

(B1)

$$R^2 \underset{R^3}{\overset{}{N}} \underset{}{\overset{N \diagup R^7}{\diagdown}} \underset{R^5}{\overset{}{N}} R^6$$

(B2)

$$\underset{Y}{\overset{X}{\diagup}} \underset{N}{\overset{N}{\diagdown}} A$$

wherein
X is —$(CH_2)_n$—, where n is an integer from 2 to 4;
Y is —$(CH_2)_m$—, where m is an integer from 2 to 5;
A is $CH_2$, NH or NR', where R' is $C_1$-$C_4$-alkyl or acyl; preferably $C_1$-$C_4$-alkyl;
$R^2$, $R^3$, $R^5$ and $R^6$ each independently is hydrogen, $C_1$-$C_4$-alkyl or $C_3$-$C_6$-cycloalkyl; preferably hydrogen or $C_1$-$C_4$-alkyl; with a provisio that all four of $R^2$ $R^3$, $R^5$ and $R^6$ are not hydrogen, and
$R^7$ is H, $C_1$-$C_4$-alkyl or $C_3$-$C_6$-cycloalkyl; preferably H or $C_1$-$C_4$-alkyl.

The amidine bases are preferably selected from 1,8-diazabicyclo[5,4,0]undec-7-en (DBU) and 1,5-diazabicyclo[4,3,0]non-5-ene (DBN).

According to one embodiment, the organic base is 1,8-diazabicyclo[5,4,0]undec-7-en (DBU).

According to another embodiment, the organic base is 1,5-diazabicyclo[4,3,0]non-5-ene (DBN).

The guanidine bases are preferably selected from cyclic guanidines, such as 1,5,7-triazabicyclo[4,4,0]dec-5-ene (TBD), 7-methyl-1,5,7-triazabicyclo[4,4,0]dec-5-ene (MTBD); and alkyl guanidines, such as tetra-methyl guanidine (TMG), tetra-butyl guanidine, penta-methyl guanidine, penta-butyl guanidine and N'-butyl-N'',N''-dicyclohexylguanidine.

According to one embodiment, the organic base is 1,5,7-triazabicyclo[4,4,0]dec-5-ene (TBD).

According to another embodiment, the organic base is 7-methyl-1,5,7-triazabicyclo[4,4,0]dec-5-ene (MTBD).

According to another embodiment, the organic base is tetra-methyl guanidine (TMG).

According to another embodiment, the organic base is tetra-butyl guanidine.

According to another embodiment, the organic base is penta-methyl guanidine.

According to another embodiment, the organic base is penta-butyl guanidine.

According to another embodiment, the organic base is N'-butyl-N'',N''-dicyclohexyl guanidine.

The organic base is used in catalytic amounts. The molar ratio of the organic base and compound (II) is generally in the range from 0.001:1 to 0.3:1, preferably from 0.005:1 to 0.25:1, more preferably from 0.01:1 to 0.2:1, most preferably from 0.05:1 to 0.2:1. The molar ratio of the organic base to compound (II) can also be in the range from 0.1:1 to 0.15:1.

The reaction of step (i) is carried out in an inert organic solvent. The inert organic solvent preferably has a water solubility of at maximum 50 g/L. Examples of suitable solvents are: aliphatic hydrocarbons containing 5 to 10 carbon atoms, for example n-pentane, n-hexane, n-heptane, n-octane, n-nonane, n-decane and their isomers, petroleum ether, cyclohexane, and methylcyclohexane; aromatic hydrocarbons, for example benzene, toluene, ethylbenzene, cymene, mesitylene, o-xylene, m-xylene, and p-xylene; halogenated aromatic hydrocarbons, for example monochlorobenzene, 1,2-dichlorobenzene, 1,3-dichlorobenzene and 1,2,4-trichlorobenzene; ethers, for example diethyl ether, methyl-tert-butyl ether; esters such as alkyl actates for example ethyl acetate, butyl acetate, iso-propyl acetate; halogenated aliphatic solvents, for example dichloromethane ($CH_2Cl_2$), tetrachloroethane ($CCl_4$), 1,2-dichloroethane; or any mixture of the above-mentioned solvents. Preferably the solvent is selected from halogenated aliphatic solvents, in particular from dichloromethane, tetrachloroethane, 1,2-dichloroethane or any mixture thereof or from halogenated aromatic hydrocarbons, for example monochlorobenzene, 1,2-dichlorobenzene, 1,3-dichlorobenzene and 1,2,4-trichlorobenzene or any mixture thereof.

According to one specific embodiment, the solvent is 1,2-dichloroethane.

According to one specific embodiment, the solvent is monochlorobenzene.

The pH of the reaction mixture in step (i) is usually kept in the range between 10 and 14, preferably between 11 and 14, more preferably between 12 and 14.

The reaction is usually carried out at a temperature between −10 and 100° C., preferably between 0 and 70° C., most preferably between 10 and 20° C., in particular between 15 and 30° C.

The order of adding the reagents to the reaction mixture is variable.

According to one embodiment, compound (II) is added to the bases. The addition of compound (II) can be done in one portion or gradually, e.g. dropwise or in several portions. According to one embodiment, the addition is made in one portion. According to another embodiment the addition is made gradually, e.g. dropwise or in several portions. The bases are preferably partially or completely dissolved in sufficient solvent and stirred during the addition of compound (II).

According to another embodiment, the bases are added to compound (II). The bases can be added separately, e.g. subsequently or in parallel, or in form of a mixture thereof. The addition can be done in one portion or gradually, e.g. dropwise or in several portions. According to one embodiment, the addition is made in one portion. According to another embodiment the addition is made gradually, e.g. dropwise or in several portions. The compound (II) is preferably dissolved in sufficient solvent and stirred during the addition of bases.

According to another embodiment, the inorganic base is added to the mixture of compound (II) and organic base. The addition can be done in one portion or gradually, e.g. dropwise or in several portions. According to one embodiment, the addition is made in one portion. According to another embodiment the addition is made gradually, e.g. dropwise or in several portions. The compound (II) and an organic base are preferably dissolved in sufficient solvent and stirred during the addition of inorganic base.

According to another embodiment, the inorganic base and compound (II) are added to the organic base. The inorganic base and compound (II) can be added separately, e.g. subsequently or in parallel, or in form of a mixture thereof. If added in parallel, the pH of the resulting mixture is preferably kept constant. The addition can be done in one portion or gradually, e.g. dropwise or in several portions. According to one embodiment, the addition is made in one portion. According to another embodiment the addition is made gradually, e.g. dropwise or in several portions. The organic base is preferably dissolved in sufficient solvent and stirred during the addition of inorganic base and compound (II).

After step (i), a work-up of the reaction mixture can be carried out or the reaction mixture can be forwarded to the next step without any work-up.

The work-up can be done by procedures known to the person skilled in the art. For example, after completion of the reaction the water is added, and the organic phase is separated. Thereafter, the organic phase is washed with an aqueous acidic solution, for example aqueous HCl, and then optionally with water. Then the solvent is removed from the separated organic phases. If desired, the organic base, which was washed out from the organic phase by the acidic solution, can be recycled and returned to step (i).

The starting compound (II) can be prepared by (ii) reacting a compound of formula (III)

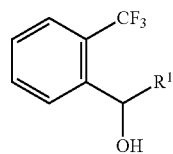

(III)

wherein R$^1$ is as defined for compound of formula (I)

with the nitric acid, optionally in the presence of the sulfuric acid or oleum, wherein the nitric acid is used in an amount of 2 to 20 mole equivalents per 1 mole of the compound (III).

In the step (ii) compound (A) is formed as an intermediate compound.

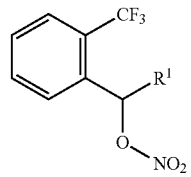

(A)

The compounds (III) are commercially available or can be synthesized as known to the skilled person, e.g. from Polymer 52, (2011), 949-953.

The step (ii) can be carried out batchwise or continuously. According to one embodiment, it is carried out batchwise. According to another embodiment, it is carried out continuously.

Nitric acid preferably has a concentration of at least 20 mol %. Usually it has a concentration of from 20 to 100 mol %, preferably from 60 to 100 mol %, more preferably from 80 to 100 mol %, most preferably from 90 to 100 mol %, particularly preferably from 95 to 100 mol %. It can contain dissolved nitrogen dioxide or be essentially free thereof. Essentially free means that it contains 0.5 mol % or less of dissolved nitrogen dioxide.

According to one specific embodiment, the nitric acid is a red fuming nitric acid.

According to another specific embodiment, the nitric acid is a white fuming nitric acid (also called 100% nitric acid).

According to another specific embodiment, the nitric acid is prepared in situ by contacting a nitrate salt, such as NaNO$_3$ or KNO$_3$ with the sulfuric acid.

The nitric acid is usually used in an amount of from 2 to 20 mole equivalents per 1 mole of compound (III), preferably from 2 to 10 mole equivalents per 1 mole of compound (III), more preferably from 2 to 8 mole equivalents per 1 mole of compound (III), most preferably from 2 to 4 mole equivalents per 1 mole of compound (III), particularly preferably from 2.1 to 2.5 mole equivalents per 1 mole of compound (III).

If the step (ii) is carried out batchwise, the nitric acid is preferably used in an amount of from 2 to 8 mole equivalents per 1 mole of compound (III), preferably from 2 to 6 mole equivalents per 1 mole of compound (III), more preferably from 2 to 3.5 mole equivalents per 1 mole of compound (III), most preferably from 2 to 3 mole equivalents per 1 mole of compound (III), particularly preferably from 2.1 to 2.5 mole equivalents per 1 mole of compound (III).

If the step (ii) is carried out continuously, the nitric acid is preferably used in an amount of from 2 to 20 mole equivalents per 1 mole of compound (III), preferably from 2 to 16 mole equivalents per 1 mole of compound (III), more preferably from 2 to 12 mole equivalents per 1 mole of compound (III), most preferably from 2 to 10 mole equivalents per 1 mole of compound (III), particularly preferably from 2 to 8 mole equivalents per 1 mole of compound (III).

The reaction can be carried out in the presence of the sulfuric acid or oleum.

According to one embodiment, the reaction is carried out in the presence of oleum.

According to another embodiment, the reaction is carried out in the presence of the sulfuric acid.

The sulfuric acid suitable for the present invention preferably has a concentration of at least 50 mol %. Usually it has a concentration of from 50 to 100 mol %, preferably from 70 to 100 mol %, more preferably from 80 to 100 mol %, most preferably from 90 to 100 mol %, particularly preferably from 95 to 100 mol %.

The sulfuric acid, if added, is usually used in an amount of from 2 to 40 mole equivalents per 1 mole of compound (III), preferably from 3 to 30 mole equivalents per 1 mole of compound (III), more preferably from 5 to 20 mole equivalents per 1 mole of compound (III), most preferably from 5 to 10 mole equivalents per 1 mole of compound (III), particularly preferably from 5 to 7 mole equivalents per 1 mole of compound (III).

The molar ratio of the nitric acid to the sulfuric acid is usually from 1:1 to 1:20, preferably from 1:1 to 1:15, more preferably from 1:1 to 1:10, most preferably from 1:1 to 1:8, particularly preferably from 1:1 to 1:4. According to a specific embodiment, the ratio is from 1:1 to 1:2. According to a further specific embodiment, the ratio is 1:1.

The nitration according to the present invention is can be carried out at a room temperature, e.g. at 20 to 25° C. It is, however, can be carried out at elevated or reduced temperatures, usually at −30 to 80° C., preferably at −15 to 60° C., more preferably at 0 to 50° C., most preferably at 5 to 45° C., particularly preferably from 10 to 40° C.

The reaction can be carried out with or without a solvent.

According to one embodiment, the reaction is carried out without a solvent.

According to another embodiment, the reaction is carried out in a solvent. Suitable solvents are selected from halogenated aliphatic solvents, such as dichloromethane ($CH_2Cl_2$), chloroform ($CHCl_3$), tetrachloroethane ($CCl_4$), 1,2-dichloroethane or any mixture of the abovementioned solvents. Preferably the solvent is selected from dichloromethane, chloroform, tetrachloroethane, 1,2-dichloroethane or any mixture thereof. Alternatively, the excess of $H_2SO_4$ or the excess of oleum can be used as a solvent.

According to one specific embodiment, the solvent is dichloromethane.

According to another specific embodiment, the solvent is chloroform.

According to another specific embodiment, the solvent is tetrachloroethane.

According to another specific embodiment, the solvent is 1,2-dichloroethane.

According to another specific embodiment, the excess of $H_2SO_4$ is used as a solvent.

According to another specific embodiment, the excess of oleum is used as a solvent.

According to one specific embodiment, in the step (ii)
a) the compound (III) is first reacted with at least 1 mole equivalent of the nitric acid per 1 mole of the compound (III) to obtain the intermediate compound (A)

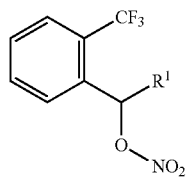

(A)

b) the water is removed from the reaction mixture and
c) the compound (A) is further reacted with 1 to 2.5 mole equivalents of the nitric acid per 1 mole of the compound (A) to obtain the compound (II).

The amount of the nitric acid used in step (ii) a) is preferably from 1 to 15 mole equivalents per 1 mole of compound (III), more preferably from 1 to 10 mole equivalents per 1 mole of compound (III), most preferably from 1 to 5 mole equivalents per 1 mole of compound (III), particularly preferably from 1 to 2.5 mole equivalents per 1 mole of compound (III), specifically from 1 to 1.5 mole equivalents per 1 mole of compound (III).

In the step (ii) b) the water can be removed as known to the skilled person. For example, it can be done by extracting the intermediate compound (A) with a water immiscible organic solvent, like halogenated aliphatic solvents as described above. If the reaction is carried out in a such halogenated aliphatic solvent, the organic phase can be separated from the aqueous phase as known to the skilled person. Alternatively, the stoichiometric amount of oleum can be added to the reaction mixture.

Water to be removed in the step (ii) b) includes the water formed during the reaction in the step (ii) a) and, in case aqueous solutions of nitric and/or sulfuric acids were employed in the step (ii) a), also the water from that aqueous solutions.

According to one specific embodiment, after the step (ii) a) is finished, in step (ii) b) the excess of nitric acid and, if any, sulfuric acid or oleum is removed from the reaction mixture together with the water.

The order of adding the reagents to the reaction mixture is variable.

According to one embodiment, the nitric acid is optionally pre-mixed with the sulfuric acid or oleum and then added to compound (III). The acid(s) can be added to the reaction mixture in one portion or gradually. According to one embodiment, the addition is carried out in one portion. According to another embodiment, the addition is carried out gradually. Gradual addition is preferred.

According to another embodiment, compound (III) is added to the nitric acid being optionally pre-mixed with sulfuric acid or oleum. The compound (III) can be added to the reaction mixture in one portion or gradually. According to one embodiment it is added to the reaction mixture in one portion. According to another embodiment it is added to the reaction mixture gradually. Gradual addition is preferred.

After step (ii), a work-up of the reaction mixture can be carried out by procedures known in a general manner to the person skilled in the art. For example, the reaction mixture is diluted with water or ice and the aqueous phase is extracted with a suitable solvent, e.g. toluene or o-xylene. If the reaction is run in the presence of halogenated organic solvents, the organic phase containing the product can be separated directly from the acid(s). The organic phases can be washed with water to remove residual acid(s), if necessary. The raw product obtained after evaporation of the solvent(s) can directly be used in a further step, if desired.

However, the raw product can also be further worked up and/or purified as generally known to the skilled person. Since compounds (II) are shock sensitive, it is preferred to forward them to step (i) without removing organic solvent. If necessary, the solution can be concentrated prior to forwarding it to step (ii). Preferably, the compound (II) remains dissolved.

The process can further comprise a further step (iii) according to which the excess of the nitric acid (and optionally sulfuric acid or oleum) is separated from the reaction mass after step (ii) is finished and returned back to the nitration step (ii). If necessary, prior to returning the separated acid(s) to step (ii) the concentration of said acid(s) can be adjusted to reach the initial concentration.

According to one specific embodiment, the excess of the nitric acid (and optionally sulfuric acid or oleum) is returned to step (ii) a).

The separation can be carried out by procedures known in a general manner to the person skilled in the art. The separates are then treated with oleum or sulfur trioxide in order to remove the water formed during the reaction and achieve the initial concentration of the sulfuric acid. The recycled concentrated sulfuric acid can be reused in the production process.

In one embodiment the invention also relates to the process for preparation of compound (IV)

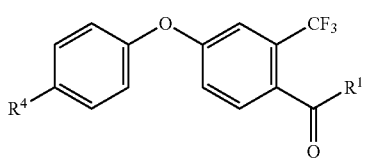

(IV)

wherein $R^1$ is $C_1$-$C_4$-alkyl;
comprising the following steps:
(i) preparing the compound (I) as described herein;
(iii) reacting the compound (I) with a phenol derivative of formula (V)

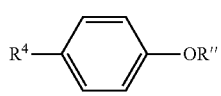

(V)

wherein
R'' is hydrogen or an alkali metal ion;
$R^4$ is halogen;
in the presence of a base.

R'' in formula (V) is hydrogen or an alkali metal cation, preferably Na or K.

$R^4$ in formula (V) is halogen, preferably F or Cl, in particular Cl.

Compounds (V) can be synthesized as known to the skilled person or are also commercially available.

If R'' in formula (V) is hydrogen, the reaction is carried out in the presence of a base. The base can be organic or inorganic base.

According to one embodiment, the base used in step (iii) is an inorganic base. Examples of suitable inorganic bases are hydroxides, carbonates, hydrocarbonates, phosphates and hydrophosphates of alkali or earth alkali metals or any mixtures thereof. Examples of the suitable inorganic bases are NaOH, KOH, CsOH, $Na_2CO_3$, $K_2CO_3$, $Cs_2CO_3$, $NaHCO_3$, $KHCO_3$, $Na_3PO_4$, $K_3PO_4$, $Na_2HPO_4$, $K_2HPO_4$, $NaH_2PO_4$, $KH_2PO_4$.

The inorganic base is preferably selected from NaOH, KOH, CsOH, $Na_2CO_3$, $K_2CO_3$ and $Cs_2CO_3$, more preferably from $Na_2CO_3$, $K_2CO_3$ and $Cs_2CO_3$. According to one specific embodiment, the inorganic base is $Na_2CO_3$. According to another specific embodiment, the inorganic base is $K_2CO_3$. According to another specific embodiment, the inorganic base is $Cs_2CO_3$.

The hydroxides and carbonates can be used alone or in the presence of 0.05-0.2 equivalents of CsF or CsCl per 1 equivalent of the hydroxide or carbonate base.

According to another embodiment, the base used in step (iii) is an organic base. Examples of suitable organic bases are alkoxides, acetates, tertiary amines, pyridine, substituted pyridines, or any mixture thereof.

Examples of suitable alkoxides are $NaOCH_3$, $KOC(CH_3)_3$ and the like.

According to another specific embodiment the organic base is selected from acetates. Examples of suitable acetates are $CH_3COONa$, $CH_3COOK$, $CH_3COOCs$.

Examples of suitable tertiary amines are tri-($C_1$-$C_6$)-alkylamines such as trimethylamine, triethylamine, tributylamine and N,N-diisopropylethylamine; di-($C_1$-$C_6$)-alkyl-phenylamines such as N,N-dimethylaniline and N,N-diethylaniline; N-methyl imidazole, N,N-dimethylaminopyridine and the like.

Examples of suitable substituted pyridines are collidine, lutidines, picolines, N,N-dimethylaminopyridine and the like.

The base can be used in solid form or as a solution, e.g. as aqueous solution.

The molar ratio of the base to compound (III) is generally from 0.5:1 to 4:1, preferably from 0.5:1 to 3.5:1, more preferably from 1:1 to 3:1, most preferably from 1:1 to 2:1.

The process step (iii) according to the present invention can be carried out in the presence of a catalyst. The catalyst is preferably a Cu(I), Cu(II) or Fe(III) catalyst. Examples of suitable catalysts are Cu(I)Cl, Cu(II)Cl$_2$, $CuSO_4.5H_2O$, Cu(OAc)$_2$ and FeCl$_3$. According to one specific embodiment the catalyst is Cu(OAc)$_2$.

The molar ratio of the catalyst to compound (III) is generally from 0.005:1 to 0.5:1, preferably from 0.075:1 to 0.4:1, more preferably from 0.01:1 to 0.3:1, most preferably from 0.05:1 to 0.1:1.

Examples for appropriate solvents for step (iii) of the inventive process are aprotic organic solvents such as for example dimethyl formamide (DMF), N-methyl pyrrolidone (NMP), dimethyl imidazolidinone (DMI), toluene, o-xylene, m-xylene, p-xylene; ethers such as monoglyme or diglyme; dimethylactamide (DMA), DMSO and any mixtures thereof. In particular DMF, NMP, toluene and DMA or any mixtures, more specifically DMF, are particularly suitable.

According to one specific embodiment, the solvent used in step (iii) contains not more than 3 eq DMF in relation to 1 eq of the phenol of formula (IV), preferably not more than 2.8 eq to 1 eq of the phenol of formula (IV), more preferably not more than 2.6 eq to 1 eq of the phenol of formula (IV), most preferably not more than 2.4 eq to 1 eq of the phenol of formula (IV), specifically not more than 2.2 eq DMF to 1 eq of the phenol of formula (IV).

The reagents for step (iii) are preferably added at ambient temperature and the reaction temperature is then elevated, wherein the reaction temperature after the reagents have been added is preferably held at a maximum of 150° C., in particular at a maximum of 140° C., more preferably at a maximum of 130° C. Generally, it is preferred to have a reaction temperature of 20° C. to 135° C., in particular 50° C. to 135° C., more particularly 100° C. to 130° C.

After step (iii), a work-up of the reaction mixture can be carried out by procedures known in a general manner to the person skilled in the art. Generally, water is added and the aqueous phase is extracted with a suitable solvent, e.g. toluene or o-xylene. The raw product obtained after evaporation of the solvent(s) can directly be used in a further step, if desired. However, the raw product can also be further worked up and/or purified as generally known to the skilled person.

According to one embodiment of the invention, after completion of the reaction, most of the solvent (e.g. DMF or toluene) is removed from the reaction mixture, preferably under reduced pressure. Then, a suitable organic solvent, such as, for example, toluene or o-xylene, is added together with water. According to the inventive process, it may be favorable to carry out one to three, preferably two extractions of the aqueous phase.

The invention is illustrated by the following examples without being limited thereto or thereby.

Experimental Part

HPLC-method: Agilent 1200; column: Hailo C-18 150× 4.6 mm; mobile phase A: acetonitrile, mobile phase B: $H_2O$+0.5% 0.5 mol/L $H_2SO_4$; flow 1.0 mL/min; gradient: 0 min 80% B—15 min 22% B—18 min 0% B—20 min 80% B; temperature 30° C., wavelength 230 nm.

Compound (I), $R^1$=$CH_3$ is at 10.1 min.
Compound (II), $R^1$=$CH_3$ is at 13.6 min.

EXAMPLE 1

Synthesis of Compound (II), $R^1$=$CH_3$ 12.5 mL 100% nitric acid (0.30 mol) was treated with 25 mL 96% sulfuric acid (0.47 mol) with cooling. 2.9 g molten α-methyl-2-(trifluoromethyl)-benzyl alcohol (15 mmol) was added to the mixture within 10 min while keeping the temperature at 0-5° C. After 15 min a solid precipitated from the mixture. The entire mixture was poured into 250 ml cold water and the product extracted with 50 mL $CH_2Cl_2$. The organic phase was washed with aqueous sodium bicarbonate and water. The $CH_2Cl_2$ was removed by rotary evaporation keeping the temperature below 25° C. The product was obtained as an oil which solidified upon standing in a few minutes. Yield 4.1 g, (14.6 mmol), 97% by qualitative HPLC, essentially pure by NMR.

$^1$H-NMR: (500 MHz, $CDCl_3$): 8.58 (d, 1H, J=2.0 Hz), 8.48 (dd, 1H, J=8.6, 2.0 Hz), 7.89 (d, 1H, J=8.6 Hz), 6.32 (q, 1H, J=6.6 Hz), 1.65 (d, 3H, J=6.6 Hz) ppm.

$^{13}$C-NMR: (125 MHz, $CDCl_3$): 20.8, 76.3 (q, J=2.5 Hz), 121.9 (q, J=6.0 Hz), 122.7 (q, J=275 Hz), 127.6, 127.7, 128.7 (q, J=33.1 Hz), 145.9, 147.5

EXAMPLE 2

Synthesis of Compound (II), $R^1$=$CH_3$ 10 g 65% nitric acid (0.10 mol) was treated with 31 g 98% sulfuric acid (0.31 mol) with cooling. 5.0 g molten α-methyl-2-(trifluoromethyl)-benzyl alcohol (26 mmol) was added to the mixture while the temperature was allowed to reach 50-55° C. The mixture cooled down to 23° C. and was post-stirred for 1 h before it was poured into 65 g of cold water. The temperature reached 55° C. The precipitated product was filtered and washed with 15 g water, followed by 2×15 g 5% aqueous sodium bicarbonate solution and 2×15 g water. The product was dried at 60° C./80 mbar. Yield 6.5 g, (24.3 mmol), 97% by qualitative HPLC, essentially pure by NMR.

EXAMPLE 3

Synthesis of Compound (II), $R^1$=$CH_3$ 28.5 g 99% nitric acid (0.45 mmol) was added slowly to 105 g 98% sulfuric acid (1.05 mol) with cooling. 61.5 g 1,2-dichloroethane was added. 28.5 g α-methyl-2-(trifluoromethyl)-benzyl alcohol (0.15 mol), dissolved in 28.5 g 1,2-dichloroethane, was added within 48 min while keeping the temperature at 19-23° C. The biphasic mixture was post-stirred for 5 h. The phases were separated. The organic phase contained 98% yield of the desired product by quantitative HPLC.

EXAMPLE 4

Synthesis of Compound (II), $R^1$=$CH_3$ 18.4 g 98% sulfuric acid (184 mmol) is added to nitric acid 11.7 g 99% nitric acid (184 mmol) at 0° C. to form nitrating acid. α-methyl-2-(trifluoromethyl)-benzyl alcohol (5 g, 26.3 mmol) is dissolved in 1,2-dichloromethane (15 mL). Said solution and the nitrating acid are dosed to a continuous reactor maintained at 40° C. with a rate of an approximately 2 mL/min per solution. The reactor is rinsed with 1,2-dichloromethane (12 mL) after the dosing is finished. The combined phases are collected, the organic phase is separated and characterized via HPLC. The content of the desired product is 20.9% w/w (yield 91%).

EXAMPLE 5

Synthesis of Compound (II), $R^1$=$CH_3$

α-methyl-2-(trifluoromethyl)-benzyl alcohol (28.5 g, 150 mmol) was dissolved in 1,2-dichloroethane (90 g) and the solution cooled to 0° C. A mixture of 11.2 g nitric acid (99%, 0.18 mol, 1.2 eq) and 17.7 g sulfuric acid (98%, 0.18 mol, 1.2 eq) was added within 27 min under intensive stirring, keeping the temperature at 0-5° C. Stirring was continued for 90 min at 5° C. and the phases were separated. The upper organic phase containing α-methyl-2-(trifluoromethyl)-benzyl nitrate was left in the reactor. A mixture of 14.0 g nitric acid (99%, 0.22 mol, 1.5 eq) and 29.4 g sulfuric acid (98%, 0.30 mol, 2.0 eq) was added within 30 min under intensive stirring, keeping the temperature at 2-9° C. The mixture was post-stirred over night at 15-20° C. The phases were separated and the organic phase (109.9 g) was analyzed. The content of the desired product was 34.2% w/w (134 mmol, yield 89%).

The isolated dry product (compound (I)) is shock-sensitive.

EXAMPLE 6

Synthesis of Compound (I), $R^1$=$CH_3$ 2.1 g DBU (14 mmol, 5 mol %) was placed together with 32 g water and 55.5 g 1,2-dichloroethane (DCE) in a reaction vessel at 15° C. A solution of 1-[4-nitro-2-(trifluoromethyl)phenyl]ethyl nitrate in DCE (251.2 g, 30.5 wt %, 273 mmol) was added under vigorous stirring at a rate of 1.1 mL/min. In parallel, an aqueous solution of KOH (103 g, 50 wt %, 917 mmol, 3.36 eq) is added at such a rate that kept the pH constant at 14. After complete addition, the mixture was warmed to 20° C. and stirred overnight. 172 g water was added and the phases were separated. The organic phase was washed with aqueous sulfuric acid (35 g, 2.7 wt %, 10 mmol, 3.5 mol %). Quantitative HPLC revealed the presence of 59.0 g 1-[4-nitro-2-(trifluoromethyl)phenyl]ethanone in the organic phase (253 mmol, 93% yield).

$^1$H-NMR: (500 MHz, $CDCl_3$): 8.58 (d, 1H, J=2.1 Hz), 8.48 (dd, 1H, J=8.6, 2.3 Hz), 7.65 (d, 1H, J=8.6 Hz), 2.63 (s, 3H) ppm.

EXAMPLE 7

Synthesis of Compound (I), $R^1=CH_3$

A solution of 1-[4-nitro-2-(trifluoromethyl)phenyl]ethyl nitrate in DCE (276.4 g, 28.0 wt %, 276 mmol) was placed in a reaction vessel. 2.1 g DBU (14 mmol, 5 mol %) was added together with 32 g water at 15° C. Under vigorous stirring, an aqueous solution of NaOH (23.2 g, 50 wt %, 290 mmol, 1.05 eq) is added at such a rate that allows to keep the temperature of the reaction mixture below 20° C. After complete addition, the mixture was warmed to 20° C. and stirred for 3 h. A second portion of aqueous NaOH (11.1 g, 50 wt %, 138 mmol, 0.5 eq) was added and the mixture stirred overnight to bring the reaction to completion. 174 g water and 56 g DCE was added and the phases were separated. The organic phase was washed with aqueous sulfuric acid (35.4 g, 2.8 wt %, 10 mmol, 3.6 mol %). Quantitative HPLC revealed the presence of 62.5 g 1-[4-nitro-2-(trifluoromethyl)phenyl]ethanone in the organic phase (268 mmol, 97% yield).

COMPARATIVE EXAMPLE 1

Inorganic Base with Addition of the Phase Transfer Catalyst

A solution of 1-[4-nitro-2-(trifluoromethyl)phenyl]ethyl nitrate in DCE (7.1 g, 28.2 wt %, 7.2 mmol) was mixed with aqueous NaOH solution (1.0 g, 30 wt %, 7.5 mmol) and 0.19 g tetrabutylammonium bromide (0.6 mmol, 8 mol %). The mixture was stirred at 20° C. Qualitative HPLC showed the following composition (area %):

| | | | |
|---|---|---|---|
| 1-[4-nitro-2-(trifluoromethyl)phenyl]ethyl nitrate | Starting material | 45.3% | 13.4 min |
| 1-[4-nitro-2-(trifluoromethyl)phenyl]ethanone | Product | 39.4% | 10.1 min |
| 1-[4-hydroxy-2-(trifluoromethyl)phenyl]ethanone | Side product A | 6.0% | 6.9 min |
| 1-[4-nitro-2-(trifluoromethyl)phenyl]ethanol | Side product B | 4.9% | 9.4 min |

COMPARATIVE EXAMPLE 2

Inorganic Base Without Addition of DBU

A solution of 1-[4-nitro-2-(trifluoromethyl)phenyl]ethyl nitrate in DCE (2.4 g, 23.8 wt %, 2.0 mmol) was diluted with 4.9 g THF. Aqueous KOH solution (0.42 g, 50 wt %, 3.7 mmol) was added and the mixture stirred for 24 h at 20° C. Qualitative HPLC showed the following composition (area %):

| | | | |
|---|---|---|---|
| 1-[4-nitro-2-(trifluoromethyl)phenyl]ethyl nitrate | Starting material | 72.9% | 13.4 min |
| 1-[4-nitro-2-(trifluoromethyl)phenyl]ethanone | Product | 17.6% | 10.1 min |
| 1-[4-nitro-2-(trifluoromethyl)phenyl]ethanol | Side product B | 1.7% | 9.4 min |
| 1-[4-nitro-2-(trifluoromethyl)phenyl]ethanol | Side product C | 2.9% | 5.9 min |

EXAMPLE 8

Synthesis of Compound (IV), $R^1=CH_3$

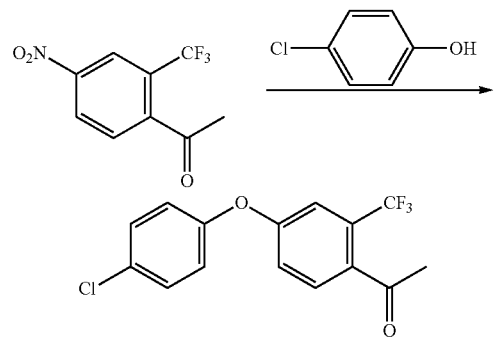

To a stirred solution of 4-nitro-2-trifluoromethyl-acetophenone (5 g, 0.02 mol) in DMF (225 mL) at 25° C. was added a potassium carbonate (2 g, 0.015 mol) and 4-chlorophenol (2.9 g, 0.022 mol). The reaction mixture was heated to 125° C. and stirred for 3 h at this temperature. Thereafter, the reaction mixture cooled down to 25° C. Water (25 mL) and toluene (25 mL) were added. The organic layer was separated, washed with aqueous NaOH (10 mL, 0.02 mol), then with water (15 mL) and concentrated under vacuum to compound give 4-(4-chlorophenyloxy)-2-trifluoromethyl-acetophenone (6 g, Yield:86.37% HPLC purity: 96.88%) as a dark brown oil.

The invention claimed is:

1. A process for the preparation of a compound of formula (I)

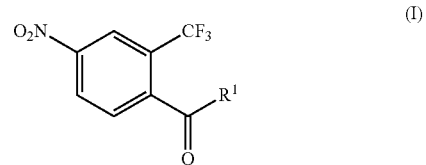

wherein $R^1$ is $C_1$-$C_4$-Alkyl;
comprising:
(i) reacting a compound of formula (II)

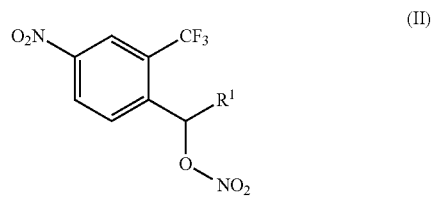

wherein $R^1$ is $C_1$-$C_4$-Alkyl;
with an aqueous solution of an inorganic base selected from hydroxides, carbonates or phosphates of alkali or earth alkali metals, or aluminium hydroxide or any mixtures thereof in the presence of an organic base selected from amidine and guanidine bases, in an inert organic solvent, wherein the reaction is heterophase and the organic base is used in an amount of 0.001 to 0.3 mol equivalents per 1 mol of compound (II).

2. The process of claim 1, wherein the organic base has a general formula (B1) or (B2),

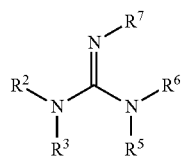
(B1)

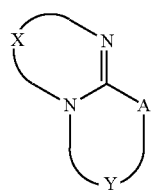
(B2)

wherein
X is —(CH$_2$)$_n$—, where n is an integer from 2 to 4;
Y is —(CH$_2$)$_m$—, where m is an integer from 2 to 5;
A is CH$_2$, NH or NR', where R' is C$_1$-C$_4$-alkyl or acyl;
R$^2$, R$^3$, R$^5$ and R$^6$ each independently is hydrogen, C$_1$-C$_4$-alkyl or C$_3$-C$_6$-cycloalkyl; with a provisio that all four of R$^2$, R$^3$, R$^5$ to R$^6$ are not hydrogen, and
R$^7$ is H, C$_1$-C$_4$-alkyl or C$_3$-C$_6$-cycloalkyl.

3. The process of claim 1, wherein the organic base is selected from the group consisting of: 1,8-diazabicyclo[5,4,0]undec-7-en (DBU), 1,5-diazabicyclo[4,3,0]non-5-ene (DBN): 1,5,7-triazabicyclo[4,4,0]dec-5-ene (TBD), 7-methyl-1,5,7-triazabicyclo[4,4,0]dec-5-ene (MTBD); and alkyl guanidines: tetra-methyl guanidine (TMG), tetra-butyl guanidine, penta-methyl guanidine, penta-butyl guanidine, and N'-butyl-N'',N''-dicyclohexylguanidine.

4. The process of claim 1, wherein the organic base is DBN or DBU.

5. The process of claim 1, wherein the organic base is DBU.

6. The process of claim 1, wherein the inorganic base is selected from the group consisting of KOH, NaOH, CsOH, K$_2$CO$_3$, Na$_2$CO$_3$, and Cs$_2$CO$_3$.

7. The process of claim 1, wherein the inorganic base is selected from KOH or NaOH.

8. The process of claim 1, wherein the inorganic base is used in an amount from 0.7 to 5 mole per 1 mole of compound (II).

9. The process of claim 1, wherein the reaction is carried out in a chlorinated aliphatic solvent.

10. The process of claim 1, wherein the reaction is carried out in 1,2-dichloroethane.

11. The process of claim 1, wherein the compound (II) is prepared by
(ii) reacting a compound of formula (III)

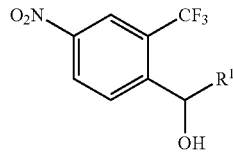
(III)

wherein R$^1$ is C$_1$-C$_4$-Alkyl;
with nitric acid, wherein the nitric acid is used in an amount of 2 to 20 mole equivalents per 1 mole of the compound (II).

12. The process of claim 11, wherein the step (ii) is carried out in a chlorinated aliphatic solvent.

13. The process of claim 12, wherein the solvent is 1,2-dichloroethane.

\* \* \* \* \*

UNITED STATES PATENT AND TRADEMARK OFFICE
CERTIFICATE OF CORRECTION

| | | |
|---|---|---|
| PATENT NO. | : 12,338,195 B2 | Page 1 of 1 |
| APPLICATION NO. | : 17/797536 | |
| DATED | : June 24, 2025 | |
| INVENTOR(S) | : Timo Frassetto et al. | |

It is certified that error appears in the above-identified patent and that said Letters Patent is hereby corrected as shown below:

In the Claims

Column 16, Line 33, Claim 11, "compound (II)." should be -- compound (III). --.

Signed and Sealed this
Twenty-eighth Day of October, 2025

John A. Squires
*Director of the United States Patent and Trademark Office*